United States Patent [19]
Luttrell et al.

[11] Patent Number: 5,117,814
[45] Date of Patent: Jun. 2, 1992

[54] DYNAMIC SPLINT

[75] Inventors: Tammy C. Luttrell, Elbert; Dan Goor, Colorado Springs, both of Colo.

[73] Assignee: Q-Motus, Inc., Colorado Springs, Colo.

[21] Appl. No.: 495,044

[22] Filed: Mar. 16, 1990

[51] Int. Cl.⁵ .............................................. A61H 1/02
[52] U.S. Cl. .............................. 128/25 R; 128/25 B; 602/16; 602/20; 602/26; 602/27
[58] Field of Search ...................... 128/80 C, 77, 80 R, 128/80 F, 80 G, 85, 88, 25 R, 25 B, 51, 52; 272/67

[56] References Cited

U.S. PATENT DOCUMENTS

| | | | |
|---|---|---|---|
| 3,323,518 | 6/1967 | Swanson | 128/25 R |
| 4,407,496 | 10/1983 | Johnson | 272/143 X |
| 4,644,938 | 2/1987 | Yates et al. | 128/25 R X |
| 4,665,900 | 5/1987 | Saringer | 128/25 R X |
| 4,669,451 | 6/1987 | Blauth et al. | 128/25 R |
| 4,772,012 | 9/1988 | Chesher | 128/26 X |
| 4,801,138 | 1/1989 | Airy et al. | 128/25 R X |
| 4,862,875 | 9/1989 | Heaton | 128/25 R X |
| 4,875,469 | 10/1989 | Brook et al. | 128/26 |

Primary Examiner—V. Millin
Assistant Examiner—J. Doyle
Attorney, Agent, or Firm—Beaton & Swanson

[57] ABSTRACT

A dynamic splint which braces any joint and particularly any body joint, and is capable of cyclically moving the joint through a programmable range of motion while accommodating normal joint component motion and triplant motion. In a preferred embodiment, an extendable cable with a cable sleeve mounted on one limb and a rotatable inner threaded cable threaded through a threaded mounting bracket on the other limb extends and contacts to cause flexing and extension of the joint.

10 Claims, 3 Drawing Sheets

DYNAMIC SPLINT

BACKGROUND OF THE INVENTION

A loss of joint flexibility is experienced by individuals recovering from neuromuscular diseases, traumatic injuries such as bone fractures, tendon and ligament tears, joint replacements and burns. In order to regain joint flexibility, it is necessary to flex or extend the joint in a repeated, controlled and quantifiable manner. It is also sometimes necessary to apply a relatively small force of a long duration or repeatedly.

Devices have been developed for either flexing or extending joints. Examples of these devices are in U.S. Pat. Nos. 4,508,111, 4,397,308, 4,485,808 and 4,538,600, all by Hepburn. These devices generally comprise upper and lower struts which attach to the limbs of the desired joint using an appropriate attachment means such as velcro or strapping. The upper and lower struts are pivotally attached to one another at the ends adjacent the joint. The pivotal attachment includes a cylindrical housing with a cam, wherein one of the struts is attached to the cam and the other bears on the cam surface through a bearing spring. Flexing or extending the joint causes a corresponding approximation or alignment of the struts relative to one another and a compression or expansion of the spring. The use of the spring allows a somewhat quantifiable and adjustable constant force to be applied to urge the flexing or extending of the joint.

The devices described in the patents named above are a great advance in that they apply a flexing or extending force on the joint rather than simply immobilizing the joint, but they have several drawbacks. One is that they do not provide for cycled flexing and extending. Recently, it has been found that cycled motion is more therapeutic than static force for treating total joint replacements and in many other therapies. Another drawback is that they pivot at a single fixed axis and move through a single plane. In contrast, the normal motion of most body joints includes pivoting at an axis that slides in relation to the joint to produce a "component motion" and that moves through at least three planes in a "triplanar motion." For example, the human knee joint does not pivot at a single axis. Instead, it pivots at an axis that slides down the kneecap, so that the lower leg actually moves away from the upper leg as the knee bends. A similar situation exists in the elbow, ankle and many other joints. The failure to accommodate this movement causes a binding of the pivot mechanism of the device and destructive pressure on the internal body joint-bearing surfaces. Accommodating this movement is particularly difficult because, not only is it complex, it also varies greatly from patient to patient.

Other devices exist which do accommodate component motion to allow normal joint response, but these devices are merely braces to limit the range of joint motion. An example of such a device is in U.S. Pat. No. 4,489,718 by Martin. This device may support the knee joint effectively and allow for limited knee motion, but it does not apply any flexing or extending force to rehabilitate the knee and increase flexibility.

SUMMARY OF THE INVENTION

The present invention is a dynamic splint which supports a joint. In particular, it can be used to support a knee or other body joint while allowing flexing and extending through the normal joint motion including component motion and triplanar motion. It may also apply a controlled and measured force to flex and extend the joint, and may do so in a predetermined cyclical manner. The force-applying mechanism is adjustable to apply a quantified force through a predetermined range of motion and at a predetermined cycle frequency. In this way, joint extension or flexing forces are applied in a single plane while allowing joint movement in all planes. This allows the dynamic splint to produce movement in the path of least resistance, rather than forcing movement along a predetermined artificial path that may be non-therapeutic or even harmful.

These principles can be accomplished in a number of ways. In a preferred embodiment of the invention, an extendable cable includes an inner cable which is rotatably mounted in a cable sleeve. At one end of the extendable cable, the cable sleeve is mounted in a cable sleeve mounting bracket releasably attached to one limb. At the other end of the extendable cable, an inner cable rotatably mounted in the cable sleeve is threaded into a threaded inner cable mounting bracket releasably attached to the other limb. Turning the inner cable with turning means threads the threaded end of the inner cable through the inner cable mounting bracket to extend the extendable cable. The extension of the extendable cable causes a bending force on the joint in the plane of the extendable cable. The direction of bending is controlled by choosing the plane of the extendable cable in relation to the joint. The extension of the extendable cable is also in the direction of joint component motion, so that the cable extension encourages the limb to follow its natural path of movement to extend the joint.

Another preferred embodiment of the invention combines the extendable cable system with a system to simultaneously produce a turning force on one limb of the joint, such as supination and pronation of the wrist with respect to the elbow. The inner cable is threaded into a bracket releasably attached in the vicinity of the wrist. The inner cable also has longitudinal teeth which engage mating teeth on a bracelet releasably attached to the wrist. In this manner, the turning of the threaded cable causes both a predetermined flexing or extending of the elbow joint and a predetermined supination or pronation of the radial ulnar forearm joint.

Another preferred embodiment utilizes an outer limb shell releasably attached to one limb of the joint, such as the lower leg, and an inner cup releasably attached to the other limb of the joint such as the heel of a foot. The inner cup is pivotally mounted in the outer limb shell with a plurality of independent flexible mounting shafts slidably mounted in slots in the outer limb shell. A rotatable cam mounted on the outer limb shell applies a force against the inner cup to flex or extend one in relation to the other. The slotted shaft-receiving mounts allow normal joint component motion through the entire range of flexing and extending of the joint.

DESCRIPTION OF THE PREFERRED EMBODIMENT

Figure 1:
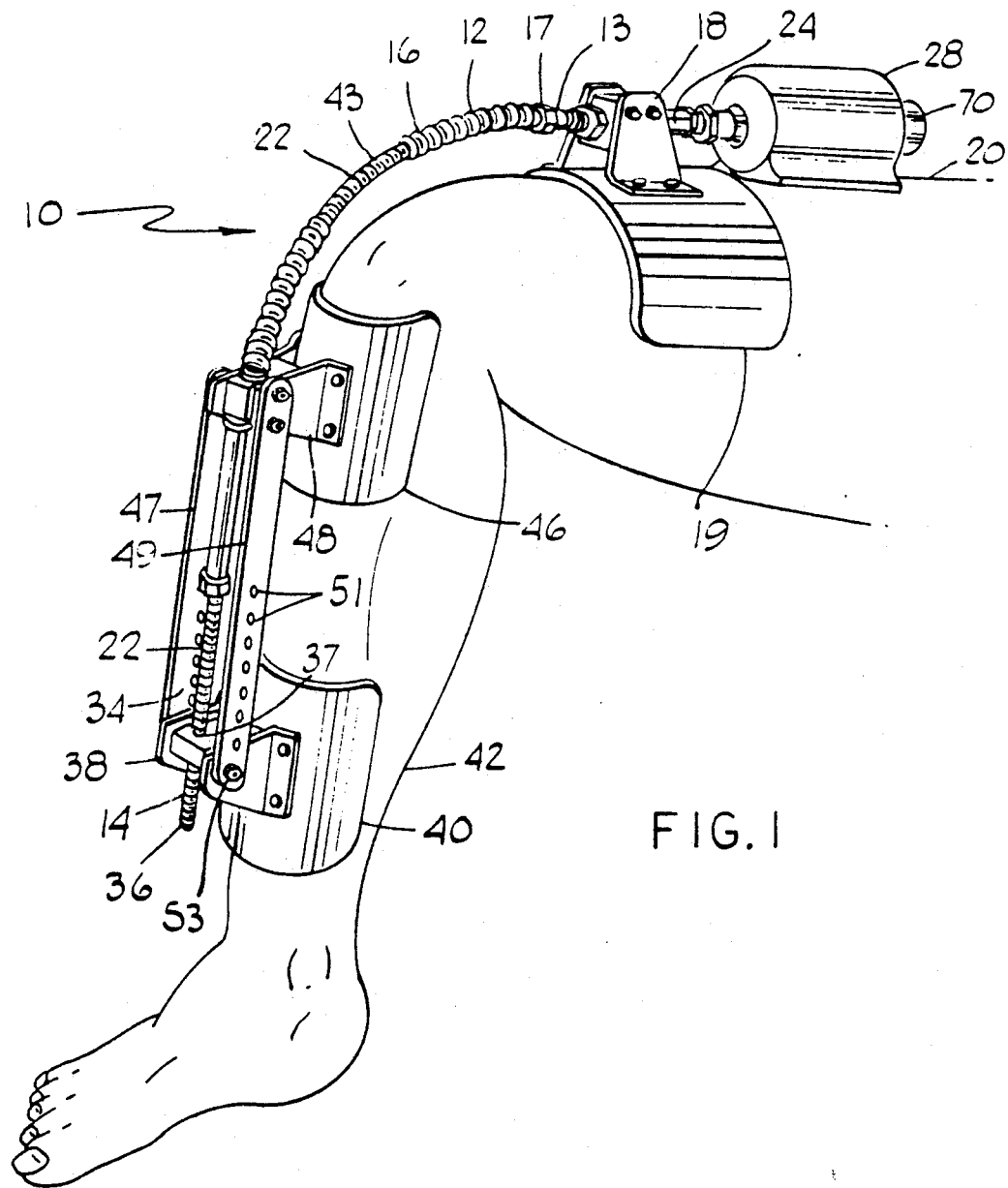
FIG. 1 is a perspective view of a first preferred embodiment of the invention, shown attached to a knee joint.

FIG. 1 shows the preferred embodiment of a dynamic splint 10 used for flexing and extending a joint such as a knee joint or other suitable joints. An extendable cable 12 has a proximal end 13 and a distal end 14. The extendable cable 12 includes a fixed cable sleeve 16 the proximal end of which 17 is attached to a cable sleeve mounting bracket 18. The cable sleeve mounting bracket 18 is releasably attached to an upper limb cuff 19 which mounts to the patient's upper limb 20 using velcro, straps, adhesive tape or other suitable releasable attachment means (not shown).

The extendable cable includes an inner cable 22. The inner cable 22 is rotatably but not slidably mounted in the cable sleeve 16 using suitable O-ring or other retainer means (not shown). The proximal end 24 of the inner cable 22 extends past the proximal end 17 of the cable sleeve 14 to allow the inner cable 22 to be turned by motor means 28.

The inner cable 22 includes threads 34 on the distal end 36. The inner cable threads 34 are into mating threads 37 in an inner cable mounting bracket 38 which is attached to a lower limb cuff 40. The lower limb cuff 40 is releasably attached to the patient's lower limb 42. The cable sleeve 16 is not attached to the inner cable mounting bracket 38.

The dynamic splint operates by turning the inner cable 22 from its proximate end 24. As the inner cable 22 is turned in one direction, the distal end 36 threads 34 are threaded through the inner cable mounting bracket 38. This effectively reduces the cable length between the inner cable mounting bracket 38 and the cable sleeve mounting bracket 18. The reduction in cable length requires an extension of the joint, since the upper limb 20 and lower limb 42 form an arc smaller than and concentric to the arc of the extendable cable 12. When the inner cable 22 is turned in the opposite direction, the distal end 36 threads 34 are unthreaded through the inner cable mounting bracket 38, to produce an effective lengthening of the extendable cable 12 and a flexing of the joint.

The cable sleeve 16 is substantially rigid to prevent any bowing of the cable as it is extended, except that a relatively short section 43 of the cable adjacent the joint is bendable to accommodate bending of the joint. This bendable section must not be too long, or it will tend to bow and will defeat the lengthening of the cable. The actual length of the bendable section will depend on the distance between the extendable cable and the limb. The bendable section may be rubber tubing, a combination of several rigid shafts with universal joint ends, or any other flexible element.

The turning of the inner cable 22 may be accomplished utilizing motor means 28 or any other source of torque energy. The motor means may be a stepper motor to allow precise control over the degree of flexing and extending of the joint as well as the amount of force to be applied to achieve that flexing and extending. Programmable control means 70 may be preset with those parameters. The control means 70 may also include calibration means to calibrate the system to the particular patient by measuring and storing the number of inner cable revolutions necessary to move the joint through the desired range of motion, to count the number of motion cycles, and to control the motion speed.

The dynamic splint of FIG. 1 may also include additional cuffs to facilitate attachment of the device onto the upper or lower limb, such as the second cuff 46 shown on the lower limb 42. The second cuff 46 includes a second cuff mounting bracket 48 that slidably engages the cable sleeve 16. The second cuff mounting bracket 48 is attached to the first cuff mounting bracket 38 with a pair of struts 47 and 49, each with a plurality of mounting holes 51 to receive a screw or shaft 53. The distance between the second cuff 46 and the first cuff 40 is adjustable by choosing from the plurality of mounting holes 51.

The apparatus may also include a hinge (not shown) to control the degree of flexing and extending of the joint. An upper hinge arm is pivotally mounted to the upper limb cuff 19, and a lower hinge arm is pivotally mounted to the first lower limb cuff 40. The two hinge arms are pivotally mounted to each other at their other ends using a rivet. The pivotal mount between the two hinge arms is also slidable through a slot in one arm that slides in relation to the rivet in the other arm. This pivotal slidable mount allows for normal joint extension and contraction during flexing and extending of the joint.

The hinge, in addition to establishing some control over the path of joint movement, may contain a safety device to limit the amount of flexing and extending of the joint. The safety device may be a micro-switch which deactivates the stepper motor or other source of torque energy when the arms reach predetermined degrees of flexing or extending.

Figure 2:
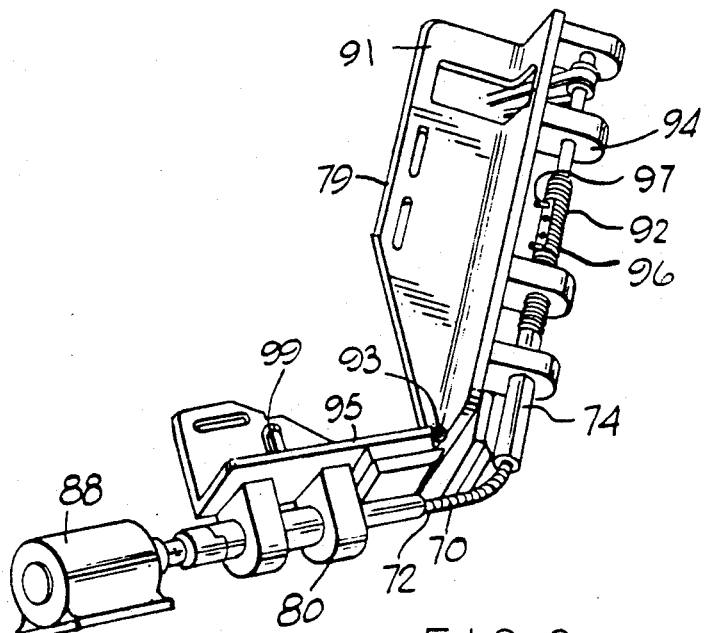
FIG. 2 is a perspective view of a second preferred embodiment of the invention, shown attached to an elbow and wrist.
Figure 3:
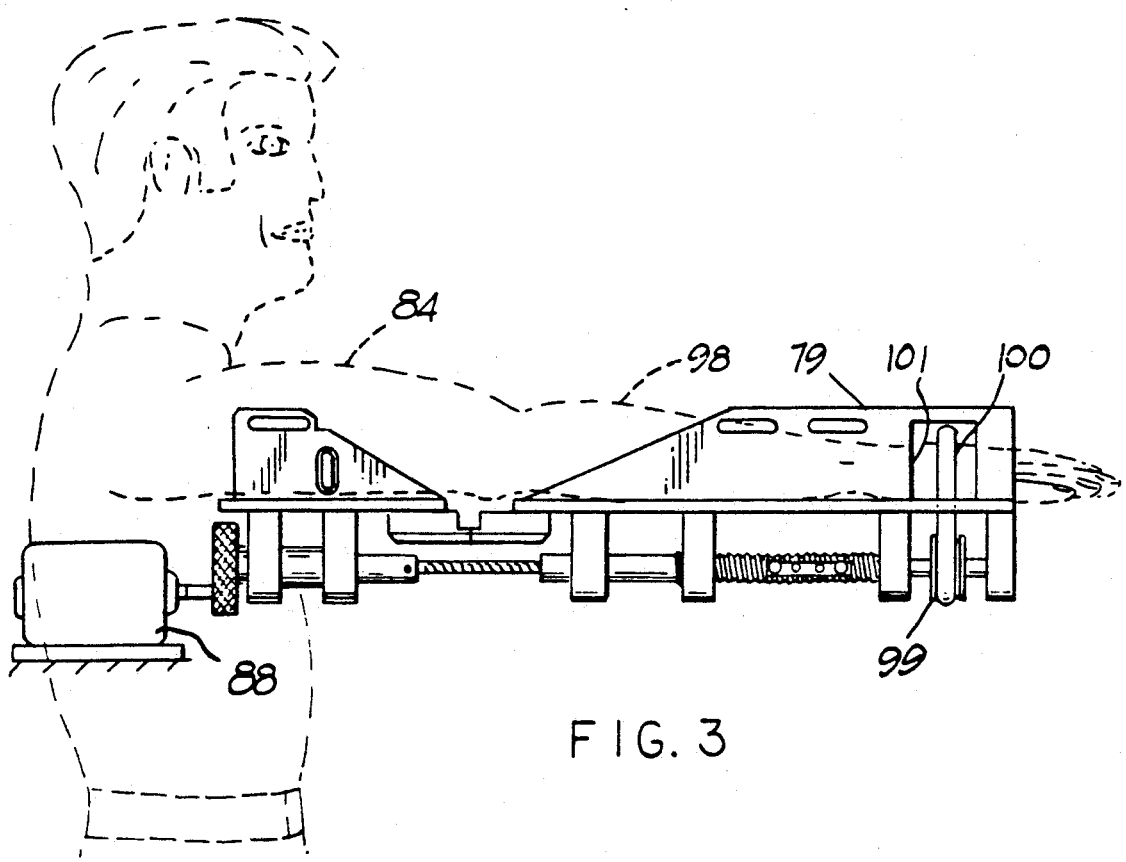
FIG. 3 is a perspective view of a third preferred embodiment of the invention, shown attached to an ankle.

Another embodiment of the invention is shown in FIGS. 2, and 3 which uses the extendable cable system of the embodiment of FIG. 1 but also provides for supination and pronation as in an elbow and wrist. The assembly includes a housing 91. The housing is hinged in the vicinity of the elbow with hinge means 93. The upper housing portion 95 is releasably attached to the patient's upper limb 84 and the lower housing portion 79 is releasably attached to the patient's lower limb 98. The embodiment uses an extendable cable 70 with a proximal end 72 and distal end 74. The extendable cable 70 proximal end 72 is mounted to an extendable cable upper mounting bracket 80 which is mounted to the upper housing portion 95. The extendable cable 70 proximal end 72 extends beyond the upper mounting bracket 80 in order to engage motor means 88. The distal end 74 of the extendable cable 70 has threads 92. The threads 92 are threaded through one or more extendable cable lower mounting brackets 94 which are attached to the lower housing portion 79.

The rotation of the inner threaded cable 84 with the motor means 88 causes the extendable cable distal end 74 to thread through the extendable cable lower mounting bracket 94. This effectively extends or reduces the cable length, thereby bending the housing 91 at the hinge 93 and extending or flexing the joint depending on the direction of rotation.

The portion of the housing that contacts the patient's upper limb 84 is equipped with rollers 99 which allow sliding of the upper limb 84 relative to the housing 91. This sliding accommodates normal joint component motion as the joint flexes and extends. The housing 91 is releasably attached to the limbs 84 and 98 with velcro, strapping or other suitable attachment means (not shown).

As shown in FIG. 3, the extendable cable distal end 74 has a set of radial holes 96 which receive one or more pins 97 which protrude from the holes. The pins act as a stop against the lower mounting brackets 94 to prevent the assembly from flexing or extending the joint too far. By adjusting the pin to different holes, the degree of flexing and extending can be controlled. The lower mounting brackets 94 may also include a microswitch or other switching means (not shown) which are activated upon contact with the pins in order to reverse the direction of flexing or extending.

The apparatus of FIG. 3 also includes a means for turning the lower limb 98 to cause supination and pronation of the wrist. A pulley 99 mounted on the extendable cable distal end 74 engages a pulley cable 100. The pulley cable 100 extends through a slot 101 in the lower housing portion 79 and is looped around the lower limb 98 so that rotation of the extendable cable 70 causes a rotation of the pulley 99 and a movement of the pulley cable 100 to rotate the lower limb 98. The pulley cable 100 is elastic so that it will extend and contract to accommodate different sized limbs. The portion of the wrist which is held by the cable pulley may be covered with a sleeve (not shown) to prevent chafing of the skin against the pulley or against the housing.

The supination and pronation of the wrist may also be accomplished with a bracelet (not shown) 96 releasably attached to the patient's lower limb with circumferential teeth which mate with longitudinal teeth on the inner cable distal end. A biased bracket attached to the lower housing portion applies a biasing force to urge the inner cable mounting bracket toward the bracelet and to engage the longitudinal teeth with the bracelet circumferential teeth. A slot in the lower housing portion 79 receives the bracelet. Thus, as the extendable cable 84 is rotated, the extendable cable extends or reduces the cable length and at the same time turns the inner lower limb bracelet to cause supination or pronation of the wrist.

The motor means 88 may include programmable control means 104 to control the degree of joint flexing and extending, the degree of pronation and supination, and the force limits.

Figure 4:
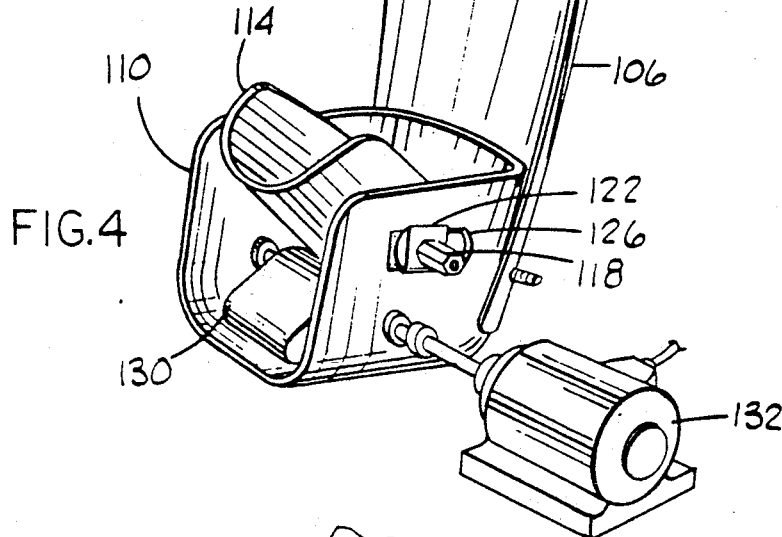
FIGS. 4-6 show an embodiment of the invention suitable for the ankle joint.
Figure 5:
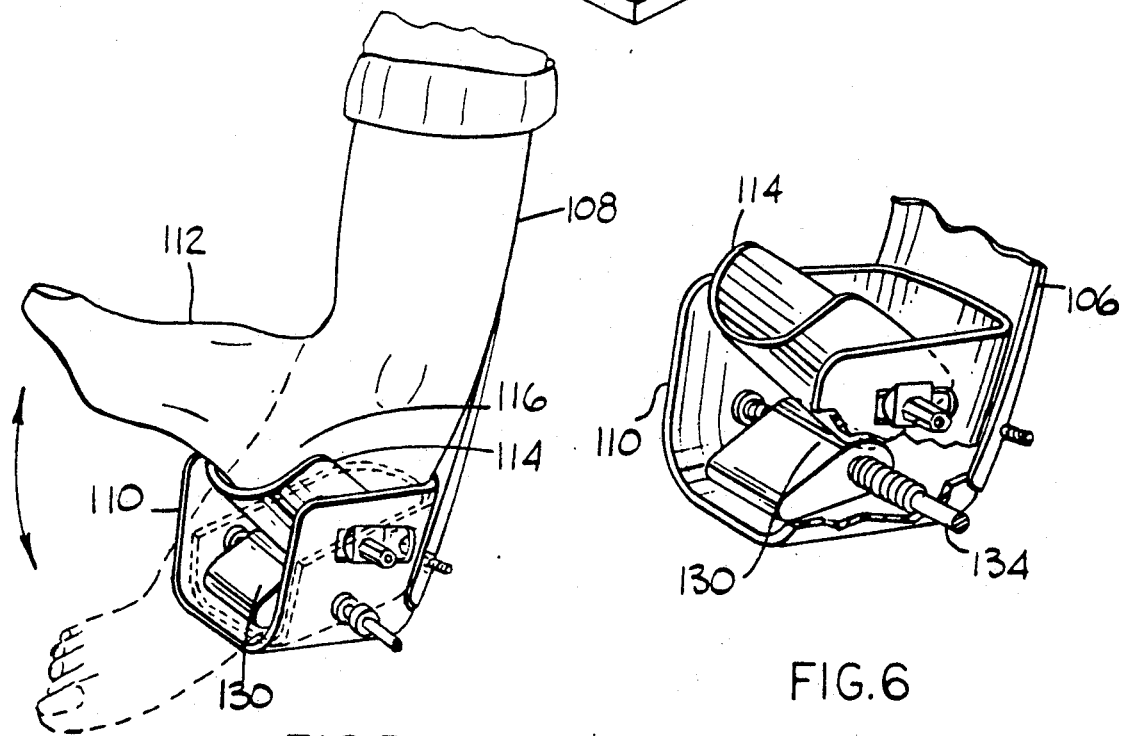
Figure 6:
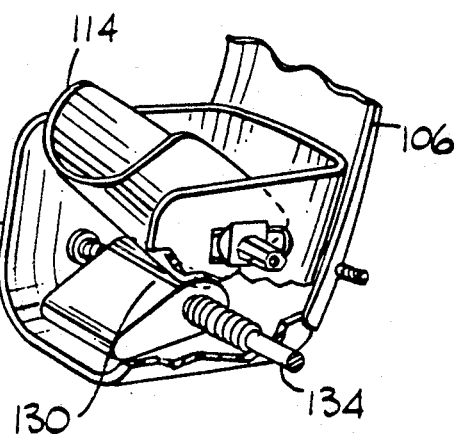

Another embodiment of the invention is shown in FIGS. 4, 5 and 6 which may be used with an ankle joint. An upper limb housing 106 is releasably attached to patient's upper limb 108. The upper limb housing 106 has a lower portion 110 which forms a shell around the lower limb 112 which is an ankle heel in the example shown in FIG. 5. Inside the lower portion shell 110 is located a heel cup 114 which is releasably attached to the patient's heel 116. The heel cup 114 is pivotally attached to the lower portion shell 110 with two independent flexible shafts 118 which extend from the interior of the lower portion shell 110 to the exterior of the heel cup 114. One of those shafts is shown in FIGS. 4, 5 and 6, and the other is similarly positioned on the opposite side of the apparatus. The flexible shafts may be ordinary helical shafts which bend in any direction but do not twist. In this manner, the heel cup 114 may pivot with respect to the upper limb housing about the flexible shafts 118. The flexibility of the shafts allow some degree of flexibility in the pivot axis to account for joint motion peculiar to each individual's anatomy.

The outer ends 122 of the flexible shafts 118 have enlarged heads which extend through the lower portion shell 110 and are retained thereby. The apertures in the lower portion shell 110 through which the flexible shafts 118 and 120 extend are slots 126 which allow the shafts to move as they pivot. This accommodates the normal biomechanical joint motion of the ankle talocrural and subtalar joints.

The heel cup 114 is positively activated to cause pivoting with respect to the upper limb housing 106 about the flexible shafts 118, with the use of a cam 130 and motor means 132. The cam is pivotally mounted on the bottom interior surface of the lower portion shell 110 on a cam pivot 134. The cam pivot 134 is activated by the motor means 132. Activation of the cam 130 applies a force to the bottom of the heel cup 114 tangential to the pivot axis of the flexible shafts 118 and 120, thereby causing a pivoting of the heel cup 114 with respect to the upper limb housing 106.

The motor means may include programmable control means to control the degree of pivoting and amount of force applied.

The apparatus of FIGS. 4, 5 and 6 may be adapted to apply a continuous static force to the ankle joint by use of a spring or other biasing means (not shown) between the back of the heel cup 114 and the inside of the lower portion 110 of the upper limb housing 106. Such an adaptation has the important benefits of allowing joint component motion and triplanar motion, as in the dynamic application.

What is claimed is:

1. An apparatus for movably bracing a joint between two members comprising:
   (a) first attachment means for releasably attaching the apparatus to one of said members and second attachment means for releasably attaching the apparatus to the other of said members;
   (b) joint flexing and extending means attached to said first and second members to apply a force urging the flexing or extending of said joint; and
   (c) supination and pronation means cooperatively engaged with said flexing and extending means, for supinating and pronating one of said members, wherein said supination and pronation means includes a pulley cable looped around one of said members and engaged with a pulley attached to said flexing and extending means.

2. An apparatus for movably bracing a joint between two members, comprising:
   (a) first attachment means for releasably attaching the apparatus to one of said members, and second attachment means for releasably attaching the apparatus to the other of said members;
   (b) a cable sleeve with two ends, one of said ends being attached to one of said attachment means;
   (c) a cable rotatably mounted in said cable sleeve and with two ends, one of said ends being threadably attached to the other of said attachment means, said cable being substantially rigid except for a flexible portion adjacent to the joint to bend as the joint bends; and
   (d) motor means attached to said cable for threading the cable through said threaded attachment, whereby the distance between the two attachment means is lengthened and shortened to flex and extend the joint.

3. The apparatus of claim 2, wherein said cable sleeve includes a substantially rigid portion adjacent to one of said attachment means and a substantially rigid portion adjacent to the other of said attachment means, said portions being separate from one another.

4. An apparatus for movably bracing a joint between two members, comprising:
   (a) first attachment means for releasably attaching the apparatus to one of said members, and second attachment means for releasably attaching the apparatus to the other of said members; and
   (b) slidable and pivotal connecting means for connecting said first and second attachment means, whereby the two attachment means can both pivot and slide with respect to one another.

5. The apparatus of claim 4, wherein said slidable and pivotal connecting means includes a first slot in one of said attachment means and a first shaft in the other attachment means, the first shaft being slidably and rotatably mounted in the first slot.

6. The apparatus of claim 5, wherein each of the two attachment means includes opposite sides, and said connecting means includes a second shaft and a second slot on the side substantially opposite the side having the first slot and first shaft, the second shaft being slidably and rotatably mounted in the second slot.

7. The apparatus of claim 4, further comprising means for applying a force urging pivoting of the two attachment means with respect to one another.

8. The apparatus of claim 7, wherein said means for applying a pivoting force includes a cam rotatably attached to one of said attachment means with a cam surface in contact with the other of said attachment means.

9. The apparatus of claim 4, wherein one of said attachment means includes a leg attachment and the other of said attachment means includes a heel cup, whereby the apparatus can be used to movably brace an ankle.

10. The apparatus of claim 8, wherein one of said attachment means includes a leg attachment and the other of said attachment means includes a heel cup, whereby the apparatus can be used to movably brace an ankle.

* * * * *